United States Patent [19]

Vásquez

[11] Patent Number: 5,444,076
[45] Date of Patent: Aug. 22, 1995

[54] PHARMACEUTICAL PREPARATION FOR TOPICAL APPLICATION

[75] Inventor: Carlos E. M. Vásquez, Buenos Aires, Argentina

[73] Assignee: Roemmers S.A.I.C.F., Argentina

[21] Appl. No.: 168,930

[22] Filed: Dec. 16, 1993

Related U.S. Application Data

[63] Continuation of Ser. No. 817,332, Jan. 6, 1992, abandoned.

[30] Foreign Application Priority Data

Nov. 26, 1990 [DE] Germany .................. 40 37 554.4

[51] Int. Cl.$^6$ ............................................. A61K 31/44
[52] U.S. Cl. .................................................. 514/352
[58] Field of Search ........................................ 514/352

[56] References Cited

U.S. PATENT DOCUMENTS

| | | | |
|---|---|---|---|
| 3,973,027 | 8/1976 | Ferrari | 424/266 |
| 4,273,777 | 6/1981 | Los | 424/263 |
| 4,407,824 | 10/1983 | Exkert | 424/329 |
| 4,559,343 | 12/1985 | Han et al. | 514/264 |

FOREIGN PATENT DOCUMENTS

| | | | |
|---|---|---|---|
| 1246446 | 12/1988 | Canada . | |
| 2935776 | 4/1981 | Germany . | |
| 8100917 | 11/1974 | Netherlands . | |
| 661474 | 12/1978 | Switzerland | A61K 31/205 |
| 1374326 | 2/1980 | United Kingdom . | |

*Primary Examiner*—Raymond Henley, III
*Attorney, Agent, or Firm*—Webb Ziesenheim Bruening Logsdon Orkin & Hanson

[57] ABSTRACT

Pharmaceutical preparations containing 1 to 10% by weight L-lysine salt of the 2-[(3-chloro-2-methylphenyl)amino]-3-pyridine carboxylic acid as active substance, 2 to 15% by weight pharmaceutically acceptable emulsifiers, 2 to 20% by weight pharmaceutically acceptable emollients, 0.01 to 0.2% by weight pharmaceutically acceptable preservation substances and the remainder water made up to 100% by weight, and possibly 0.2 to 5% by weight rubefacients, the water being correspondingly adjusted to a total of 100% by weight, are suitable for topical application to relieve/alleviate pain and/or inflammation in humans and animals.

13 Claims, 1 Drawing Sheet

PHARMACEUTICAL PREPARATION FOR TOPICAL APPLICATION

This is a continuation of application Ser. No. 07/817,332 filed on Jan. 6, 1992, abandoned.

The invention relates to pharmaceutical preparations for topical application which are preferably in the form of creams or gels and contain as active substance the L-lysine salt of the 2-[(3-chloro-2-methylphenyl-)amino]-3-pyridine carboxylic acid of the formula (I), hereinafter designated lysine clonixinate.

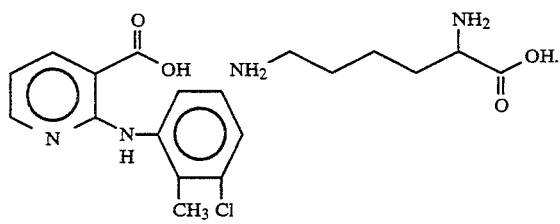

The pharmaceutical preparations are useful as topical analgesics and anti-inflammatory agents.

Drugs for oral and rectal administration and injectable solutions containing lysine clonixinate as active substance are known from the literature, for example from DE-PS No. 2,253,134 and U.S. Pat. No. 3,973,027 and/or are available on the market. These drugs develop a good analgesic and anti-inflammatory activity. However, there are cases in which they are not suitable or applicable. Thus, when a person suffers from pain in a limited area of the body, for example after a blow or knock or due to a minor accident, in the case of contusions, distortions, luxations or arthritis, arthrosis, tenalgia, bursitis, myalgia and sport injuries, a localized topical application of a substance is generally regarded as the most suitable way or the most suitable method for healing. It is also important not to apply an active substance more strongly or more weakly than is necessary to relieve or eliminate the pain or inflammation, and thus to avoid unnecessary secondary reactions or habituation to the active substances, or dependence thereon, or obtaining only slight relief. Finally, topical formulations such as creams or gels are less dangerous than tablets, in particular for self-medication, as is made possible by freely purchasable remedies. Thus, the making available of remedies for topical application which develop a mean analgesic and anti-inflammatory activity is an important problem in therapeutics.

Topical formulations containing the analgesic/anti-inflammatory agent as active substances are generally known from the literature. For example, NL-OS No. 8,100,917 (1982), CH-PS No. 651,474 (1985) and U.S. Pat. No. 4,407,824 (1983) relate to the amine salts of diclofenac. In DE-OS No. 2,935,776 (1981) as well various organic salts of anti-inflammatory medicaments are named which are suitable for topical application.

It has now been found that the L-lysine salt of 2-[(3-chloro-2-methylphenyl)amino]-3-pyridine carboxylic acid is very well suited to the preparation of pharmaceutical compositions for topical application and develops a very good effect on such an application.

DETAILED DESCRIPTION OF THE INVENTION

Figure 1:
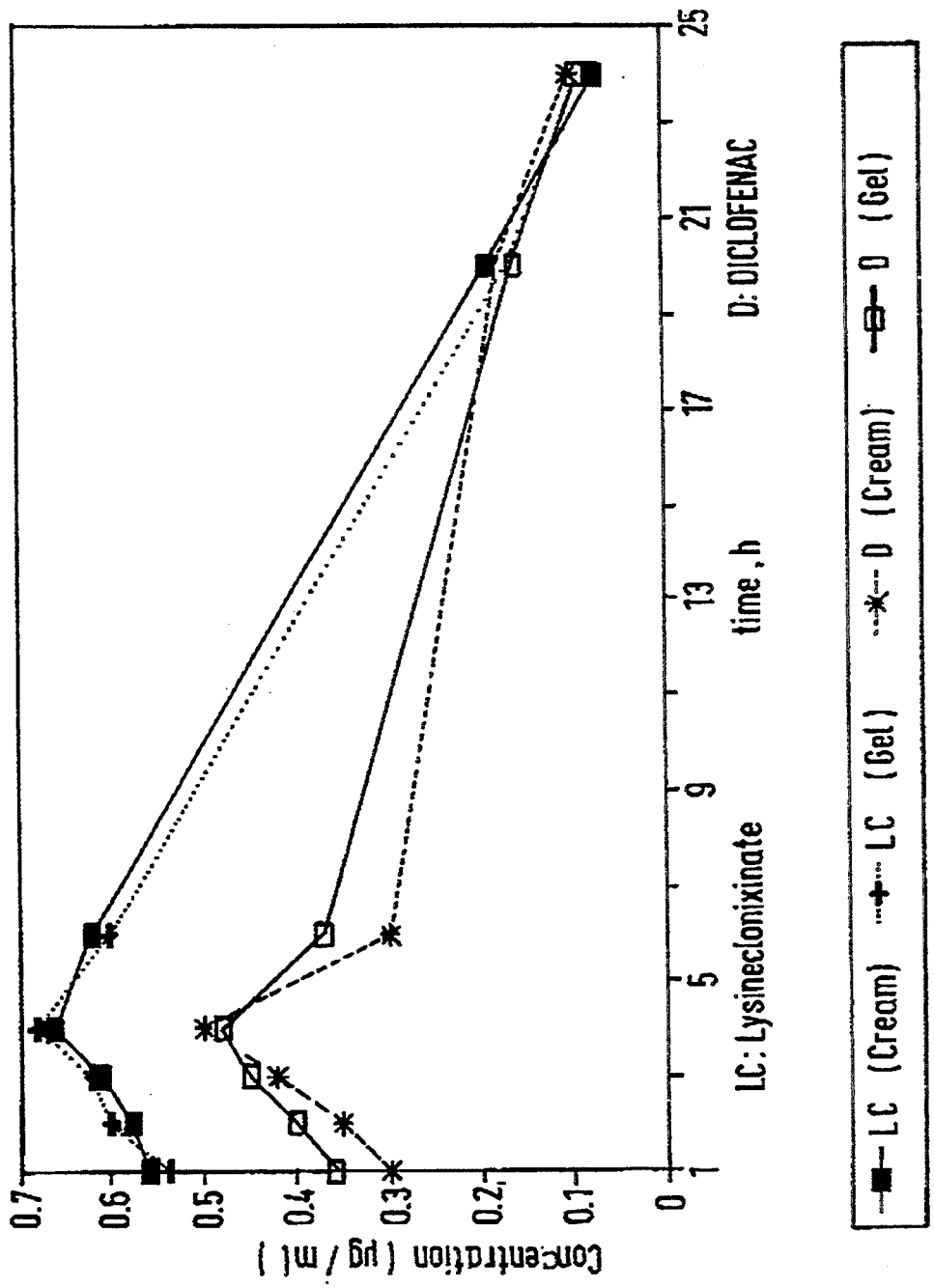
FIG. 1 is a line graph showing comparative blood concentrations resulting from separate topical administrations of diclofenac and lysine clonixinate to the skin of shaved Flemish rabbits (see Example 6 below).

The subject of the invention is therefore pharmaceutical preparations for topical application, preferably in the form of creams or gels, which with respect to the weight contain as active substance 1 to 10% by weight L-lysine salt of the 2-[(3-chloro-2-methylphenyl-)amino]-3-pyridine carboxylic acid and 2 to 15% by weight pharmaceutically acceptable emulsifiers, 2 to 20% by weight pharmaceutically acceptable emollients or softening agents, 0.01 to 0.2% by weight pharmaceutically acceptable preservation substances and water to make up 100% by weight. Possibly, these agents may also contain 0.2 to 5% by weight rubefacients and in the case of creams 3 to 18% by weight pharmaceutically acceptable lubricants or in the case of gels 0.5 to 5% by weight pH-value modifiers, the accompanying water always being adjusted to make up 100% by weight.

The pharmaceutical preparations according to the invention are distinguished by the following advantages:

local action,
rapid response/reaction due to rapid absorption,
low toxicity in uninjured or undamaged tissues or organs.

According to an preferred embodiment the pharmaceutical preparations according to the invention for topical application contain 3 to 7% by weight L-lysine salt of the 2-[(3-chloro-2-methylphenyl)amino]-3-pyridine carboxylic acid as active substance, 3 to 13% by weight pharmaceutically acceptable emulsifiers, 3 to 10% by weight pharmaceutically acceptable emollients, 0.02 to 0.1% by weight pharmaceutically acceptable preservation substances and water as remainder up to 100%. Possibly, 0.5 to 2% by weight rubefacients may also be contained therein and in the case of creams 8 to 12% by weight pharmaceutically acceptable lubricants and in the case of gels 1 to 3% by weight modifiers of the pH-value, the accompanying water always being made up to a total of 100%.

Advantageously, the emulsifiers are selected from the group of the following substances: Glyceryl monostearate, glyceryl monostearate/polyoxyethylene stearate, ketostearyl alcohol/potassium lauryl sulfate (emulsifier wax) and carbomer.

The softening agent or emollient is preferably selected from propylene glycol, glycerol, sorbite and isopropyl myristate.

As preservative agents or substance, methyl parabene, ethyl parabene and propyl parabene have proved expedient.

Menthol is advantageously used as rubefacient.

As already mentioned, the pharmaceutical preparations according to the invention are preferably brought into the galenic form of a cream or a gel.

If the pharmaceutical preparation according to the invention is to be formulated as cream, as emulsifier advantageously ketostearyl alcohol/lauryl sulfate ("emulsifier wax") is used and the lubricants are selected from the group consisting of mineral oil, vaseline and fatty acids.

If the pharmaceutical preparations according to the invention are formulated as gel, advantageously carbomer is used as emulsifier and propylene glycol as softening agent, and the modifiers for the pH-value or buffer are selected from the group consisting of sodium hydroxide, triethanol amine, trimethamine, (tris(hydroxymethyl)amino methane) and lysine.

For both creams and gels, isopropyl myristate is very well suited as softening agent or emollient.

Of the preservation agents, methyl parabene and propyl parabene are preferred.

According to the invention, the L-lysine salt of the 2-[(3-chloro-2-methylphenyl)amino]-3-pyridine carboxylic acid can be used for the preparation of a pharmaceutical composition for topical application in order to relieve or at least alleviate pain and/or inflammations in humans and animals. The following examples serve for more detailed explanation of the invention.

EXAMPLE 1

Topical pharmaceutical preparation in the form of a cream without rubefacient.

A cream was made having the following composition:
lysine clonixinate 5.0% by weight
isopropyl myristate 9.0% by weight
methyl parabene 0.1% by weight
emulsifier wax 13.0% by weight
mineral oil 10.0% by weight
water up to 100.0% by weight The lubricant, emulsifier and the emollient are melted together at 65° to 70° C. The active substance and the preservation agent are dissolved in water. The oily phase is added under constant stirring to the aqueous solution and after cooling to room temperature the desired cream is obtained.

EXAMPLE 2

Topical pharmaceutical preparation in the form of a cream with a rubefacient.

A cream of the following composition was prepared:
lysine clonixinate 5.0% by weight
isopropyl myristate 10.0% by weight
methyl parabene 0.1% by weight
propyl parabene 0.02% by weight
"emulsifier wax" 10.0% by weight
vaseline 10.0% by weight
menthol 1.0% by weight
water up to 100.0% by weight The lubricant and the emulsifier were melted together at 65°–70° C. The active substance and the preservation agent were dissolved in water. The oil phase is added under constant stirring to the aqueous solution.

Menthol was dissolved up to complete solution in the emollient.

After cooling to 40° C. the menthol solution in the emollient was added to the emulsion with constant stirring. After cooling to room temperature the desired cream was obtained.

EXAMPLE 3

Topical pharmaceutical preparation in the form of a gel without rubefacient.

A gel of the following composition was prepared:
lysine clonixinate 5.0% by weight
carbomer 3.0% by weight
propylene glycol 5.0% by weight
isopropyl myristate 3.0% by weight
glycerol 3.0% by weight
methyl parabene 0.1% by weight
propyl parabene 0.02% by weight
sodium hydroxide 1.5% by weight
water up to 100.0% by weight The active substance was dissolved in the mixture of propylene glycol and glycerol (solution A). The preservation substances were dissolved in water, the emulsifier was dispersed in the aqueous solution and the buffer (pH-modifier) was added (dispersion B). The solution A was poured over the dispersion B and finally isopropyl myristate was added.

EXAMPLE 4

Topical pharmaceutical preparation in the form of a gel with rubefacient.

A gel of the following composition was prepared:
lysine clonixinate 5.0% by weight
carbomer 3.0% by weight
propylene glycol 6.0% by weight
isopropyl myristate 3.5% by weight
methyl parabene 0.1% by weight
sodium hydroxide 2.0% by weight
menthol 1.0% by weight
water up to 100.0% by weight The active substance was dissolved in the propylene glycol and a third of the total amount of water (solution A). The preservation substance was dissolved in the remaining water and the emulsifier dispersed in said aqueous solution; thereupon, the buffer (pH-modifier) was added (dispersion B). The solution A was then poured into the dispersion B whilst stirring and finally the menthol dissolved in isopropyl myristate added. The pH-value was checked and adjusted to 8.2–8.9.

The following examples 5 and 6 will explain the advantageous use of the topical agent according to the invention compared with a conventional analgesic/antiinflammatory agent (diclofenac) both as regards the alleviation of inflammations and the absorption or takeup (through the skin).

EXAMPLE 5

Anti-inflammatory effect. Paw edema induced by carragheenin

Carragheenin in 1% dosage was administered to Wistar rats of both sexes, body weight 175–200 g, that is 0.1 ml into the paw, corresponding to the procedure adopted by Winter et al. (J. Pharmacol. and Exp. Therap. 1949, 96; 99). 30 minutes previously, in each case one of the three groups of six test animals had been treated with the following compositions: lysine clonixinate cream corresponding to example 1, 5%; 20 mg/kg; sodium diclofenac 5%, 20 mg/kg; excipient; in each case on an area of 20 cm³ on the back of the previously shaved animals. The inflammatory edema of the paw was measured with a Ugo Basile plethysmometer 3 and 5 h after the carragheenin administration. The percentage alleviation or reduction of the inflammation was determined with respect to the control group. The results are summarized in the following Table 1.

TABLE 1

| Percentage alleviation of the inflammation by the various compounds tested | | |
|---|---|---|
| Pharmaceutical | % alleviation | |
| preparation | 3 h | 5 h |
| lysine clonixinate | 50 | 48 |
| sodium diclofenac | 35 | 30 |

Example 6

Transdermal absorption. Comparative tests between a cream and a gel each containing lysine clonixinate, with corresponding commercially available products As test animals, Flemish giant rabbits having a body weight of about 3.5 kg were used which had been shaved on their backs over an area of 10 cm$^3$.

Each group contained three animals which had been treated with the following formulations and the following doses:
a) Lysine clonixinate, 5% cream, 20 mg/kg, prepared according to example 1.
b) Lysine clonixinate, 5% gel, 20 mg/kg, prepared according to example 3.
c) Sodium diclofenac, 5% cream, 20 mg/kg.
d) Diclofenac diethyl ammonium salt, 5% gel, 20 mg/kg.

Blood samples were taken from the central artery of the ear and the concentrations of the various active substances determined.

The results are shown in the following Table 2 and in the diagram attached as FIG. 1.

TABLE 2

Concentration of lysine clonixinate and diclofenac in mg/ml in the various formulations and at various times

| Pharmaceutical preparation | | time h | | | | | | |
|---|---|---|---|---|---|---|---|---|
| | | 1 | 2 | 3 | 4 | 6 | 20 | 24 |
| Lysine cloni- xinate | cream | 0,56 ± 0,11 | 0,58 ± 0,12 | 0,61 ± 0,13 | 0,66 ± 0,13 | 0,62 ± 0,14 | 0,19 ± 0,04 | 0,07 ± 0,02 |
| | Gel | 0,54 ± 0,10 | 0,60 ± 0,11 | 0,62 ± 0,12 | 0,68 ± 0,14 | 0,60 ± 0,12 | 0,17 ± 0,03 | 0,08 ± 0,02 |
| Diclo- fenac | cream | 0,30 ± 0,07 | 0,35 ± 0,08 | 0,42 ± 0,08 | 0,50 ± 0,10 | 0,30 ± 0,07 | 0,18 ± 0,04 | 0,10 ± 0,02 |
| | Gel | 0,36 ± 0,06 | 0,40 ± 0,08 | 0,45 ± 0,08 | 0,48 ± 0,09 | 0,37 ± 0,07 | 0,16 ± 0,03 | 0,09 ± 0,02 |

I claim:

1. A pharmaceutical preparation for topical application comprising:
1 to 10% by weight L-lysine salt of the 2-[(3-chloro-2-methylphenyl)amino]-3-pyridine carboxylic acid as active substance, 2 to 15% by weight pharmaceutically acceptable emulsifier, 2 to 20% by weight pharmaceutically acceptable emollient, and 0.01 to 0.2% by weight pharmaceutically acceptable preservation substance.

2. The pharmaceutical preparation according to claim 1 wherein the preparation is in a form selected from the group consisting of cream additionally containing 3 to 18% by weight pharmaceutically acceptable lubricant and gel additionally containing 0.5 to 5% by weight buffer.

3. The pharmaceutical preparation according to claim 2, comprising 3 to 7% by weight of said L-lysine salt, 3 to 13% by weight of said pharmaceutically acceptable emulsifier, 3 to 10% by weight of said pharmaceutically acceptable emollient, and 0.02 to 0.1% by weight of said pharmaceutically acceptable preservation substance.

4. The pharmaceutical preparation according to claim 3 wherein said emulsifier is selected from the group consisting of glyceryl monostearate, glyceryl monostearate/polyoxyethylene stearate, ketostearyl alcohol/sodium lauryl sulfate and carbomer.

5. The pharmaceutical preparation according to claim 4 wherein said emollient is selected from the group consisting of propylene glycol, glycerol, sorbite and isopropyl myristate.

6. The pharmaceutical preparation according to claim 5 wherein said preservation agent is selected from the group consisting of methyl paraben, ethyl paraben and propyl paraben.

7. The pharmaceutical preparation according to claim 6 wherein the preparation further includes 0.2 to 5% by weight of a rubefacient, and further wherein said rubefacient is menthol.

8. The pharmaceutical preparation according to claim 7 wherein said emulsifier is ketostearyl alcohol/sodium lauryl sulfate.

9. The pharmaceutical preparation according to claim 7 wherein said emulsifier is carbomer.

10. The pharmaceutical preparation according to claim 1 wherein said emollient is propylene glycol.

11. The pharmaceutical preparation according to claim 1 wherein said emollient is isopropyl myristate.

12. The pharmaceutical preparation according to claim 1 wherein said preservation agent is selected from the group consisting of methyl parabene or propyl parabene.

13. A method of treating pain and/or inflammation in a human or animal comprising the topical application of the L-lysine salt of 2-[(3-chloro-2-methylphenyl)amino]-3-pyridine carboxylic acid, together with at least one pharmaceutically acceptable excipient, to a human or animal in which treatment of pain and/or inflammation is desired.

* * * * *

UNITED STATES PATENT AND TRADEMARK OFFICE
CERTIFICATE OF CORRECTION

PATENT NO. : 5,444,076
DATED : August 22, 1995
INVENTOR(S) : Carlos E. M. Vasquez It is certified that error appears in the above-indentified patent and that said Letters Patent is hereby corrected as shown below:

Title page,  Item [30], delete
                Foreign Application Priority Data
          Nov. 26, 1990 [DE] Germany ... 40 37 554.4".

Signed and Sealed this

Thirteenth Day of February, 1996

Attest:

BRUCE LEHMAN

*Attesting Officer*       *Commissioner of Patents and Trademarks*